United States Patent
Schoeffel (10) Patent No.: US 9,872,748 B2
(45) Date of Patent: *Jan. 23, 2018

(54) APPARATUS FOR EVACUATION OF ROOT CANAL

(71) Applicant: Ormco Corporation, Orange, CA (US)

(72) Inventor: G. John Schoeffel, Dana Point, CA (US)

(73) Assignee: Ormco Corporation, Orange, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 14/281,639

(22) Filed: May 19, 2014

(65) Prior Publication Data

US 2014/0363793 A1    Dec. 11, 2014

Related U.S. Application Data

(63) Continuation of application No. 13/274,336, filed on Oct. 16, 2011, now Pat. No. 8,827,705, which is a
(Continued)

(51) Int. Cl.
*A61C 5/02* (2006.01)
*A61C 17/02* (2006.01)
*A61C 5/04* (2006.01)

(52) U.S. Cl.
CPC ............ *A61C 17/0208* (2013.01); *A61C 5/02* (2013.01); *A61C 5/04* (2013.01)

(58) Field of Classification Search
CPC ......... A61C 5/04; A61C 17/0202; A61C 5/02; A61C 5/023; A61C 5/026; A61C 5/062; A61C 17/0208; A61C 5/40; A61C 5/50
(Continued)

(56) References Cited

U.S. PATENT DOCUMENTS 2,173,637 A * 9/1939 Riedener ............ A61C 17/0208
600/573
3,624,907 A   12/1971 Brass et al.
(Continued)

FOREIGN PATENT DOCUMENTS

AT    179007 B    7/1954
CH    657520 A5   9/1986
(Continued)

OTHER PUBLICATIONS

Ingle, John I. and Bakland, Leif I., "Endodontics", Jun. 2002, pp. 502-503.
(Continued)

*Primary Examiner* — Yogesh Patel
(74) *Attorney, Agent, or Firm* — Wood Herron & Evans LLP (57) ABSTRACT

In an endodontic procedure, after the working of a root canal by instruments to remove material and shape the walls of the canal, irrigant is supplied via a microcannula. A vacuum is applied via a tube which is inserted partway down the root canal. The irrigant is supplied in a manner sufficient to ensure delivery to a side vent of the microcannula. The vacuum at the end of tube draws the irrigant and debris up from the apex of the root canal into the tube. The side vent may have a plurality of more round holes, a diagonal slit, or a U shaped slit, or any other shape. The vent opening should not extend more than approximately 0.75 mm from the closed spherical tip of the microcannula, it must be burr free and the opening must be smaller than the internal diameter of the microcannula.

7 Claims, 10 Drawing Sheets

Related U.S. Application Data continuation of application No. 11/629,552, filed as application No. PCT/US2005/021039 on Jun. 14, 2005, now abandoned, said application No. 11/629,552 is a continuation of application No. 11/152,942, filed on Jun. 13, 2005, now Pat. No. 7,226,288, which is a continuation-in-part of application No. 10/387,804, filed on Mar. 13, 2003, now Pat. No. 6,997,714.

(60) Provisional application No. 60/579,915, filed on Jun. 14, 2004.

(58) Field of Classification Search
USPC .................................. 433/81, 224, 80, 215
See application file for complete search history.

(56) References Cited

U.S. PATENT DOCUMENTS

| | | | |
|---|---|---|---|
| 3,804,089 A | | 4/1974 | Bridgman |
| 3,816,921 A | | 6/1974 | Malmin |
| 3,871,099 A | | 3/1975 | Kahn |
| 4,021,921 A | | 5/1977 | Detaille |
| 4,276,880 A | * | 7/1981 | Malmin ................... A61C 5/02 433/80 |
| 4,993,947 A | | 2/1991 | Grosrey |
| 5,540,587 A | | 7/1996 | Malmin |
| 5,749,727 A | | 5/1998 | Dao et al. |
| 5,807,106 A | | 9/1998 | Heath |
| 5,876,383 A | | 3/1999 | Grooters et al. |
| 6,030,212 A | | 2/2000 | Schuman et al. |
| 6,079,979 A | | 6/2000 | Riitano |
| 6,235,008 B1 | | 5/2001 | Heinzelman et al. |
| 6,390,815 B1 | | 5/2002 | Pond |
| 6,419,485 B1 | | 7/2002 | Pond |
| 6,464,498 B1 | | 10/2002 | Pond |
| 6,533,578 B2 | | 3/2003 | Segal |
| 6,638,064 B1 | | 10/2003 | Nance |
| 6,796,796 B2 | | 9/2004 | Segal |
| 6,802,829 B2 | | 10/2004 | Buono |
| 6,810,585 B2 | | 11/2004 | Hickok |
| 6,997,714 B1 | | 2/2006 | Schoeffel |
| 7,226,288 B2 | | 6/2007 | Schoeffel |
| 2002/0142260 A1 | | 10/2002 | Pond |
| 2004/0043356 A1 | | 3/2004 | Schlussel |
| 2005/0170312 A1 | | 8/2005 | Pond |
| 2005/0287498 A1 | * | 12/2005 | Schoeffel ........... A61C 17/0208 433/224 |
| 2008/0032259 A1 | * | 2/2008 | Schoeffel ....................... 433/81 |
| 2008/0160481 A1 | | 7/2008 | Schoeffel |

FOREIGN PATENT DOCUMENTS

| | | |
|---|---|---|
| DE | 860839 C | 12/1952 |
| DE | 19535349 A1 | 3/1997 |
| JP | 51-64791 B2 | 6/1976 |
| JP | 61-09849 | 1/1986 |
| JP | 64-064648 | 3/1989 |
| JP | 2003-526416 A | 9/2003 |
| JP | 2004-313659 A | 11/2004 |
| WO | 01-54608 A1 | 8/2001 |

OTHER PUBLICATIONS

Japanese Patent Office, Office Action in Japanese Patent Application No. 2011-137563 dated Jan. 22, 2013.
European Patent Office, Examination Report in EP Application No. 05759591, Apr. 24, 2012.
Canadian Patent Office, Office Action in CA Application No. 2570014, May 4, 2012.
European Patent Office, Supplemental European Search Report in EP Application No. 05759591, Dec. 14, 2011.
The International Bureau of WIPO, International Preliminary Report on Patentability in PCT Application No. PCT/US2005/021039, Oct. 26, 2006.
U.S. Patent and Trademark Office, International Search Report and Written Opinion in PCT Application No. PCT/US2005/021039, Oct. 26, 2006.
U.S. Patent and Trademark Office, Notice of Allowance in U.S. Appl. No. 13/274,336 dated Mar. 10, 2014.
U.S. Patent and Trademark Office, Office Action in U.S. Appl. No. 13/274,336 dated Jun. 12, 2013.
U.S. Patent and Trademark Office, Office Action in U.S. Appl. No. 13/274,336 dated Nov. 7, 2012.
U.S. Patent and Trademark Office, Office Action in U.S. Appl. No. 13/274,336 dated Aug. 14, 2012.

* cited by examiner

APPARATUS FOR EVACUATION OF ROOT CANAL

CROSS REFERENCE TO RELATED CASES

The present application is a continuation of U.S. application Ser. No. 13/274,336 filed Oct. 16, 2011, which is a continuation of U.S. application Ser. No. 11/629,552 filed Dec. 13, 2006, which is a 371 application of PCT/US05/021039 filed Jun. 14, 2005, which claims benefit of U.S. Provisional Patent Application Ser. No. 60/579,915 filed Jun. 14, 2004, and U.S. application Ser. No. 11/152,942 filed Jun. 13, 2005, which also claims benefit of U.S. Provisional Patent Application Ser. No. 60/579,915 and is a continuation-in-part of U.S. application Ser. No. 10/387,804, filed Mar. 13, 2003, the disclosures of which are incorporated by reference herein in their entirety.

TECHNICAL FIELD

The invention is in the field of endodontics, more particularly methods and apparatus used during root canal procedures.

BACKGROUND

Figure 2A:
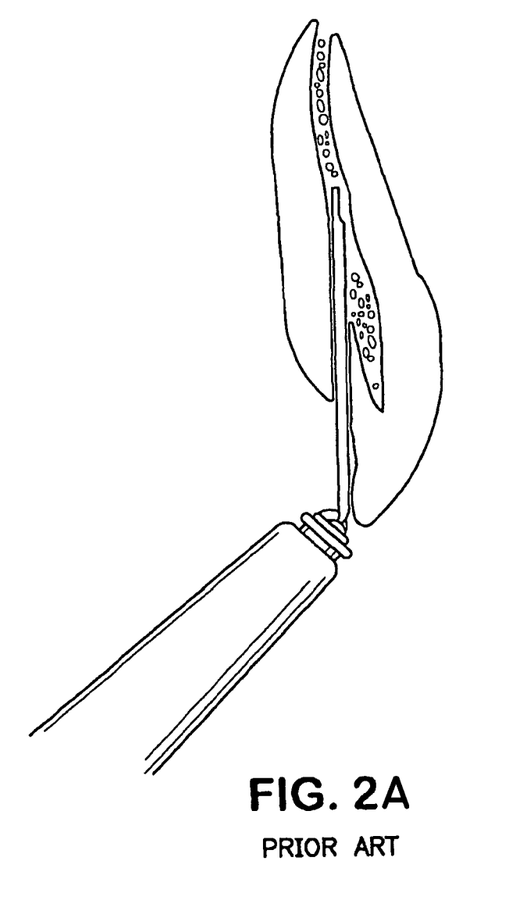
FIGS. 2A and 2B show a prior art endodontic irrigation system.
Figure 2B:
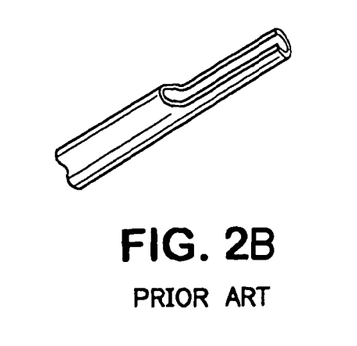

To preserve a tooth that has or could develop a diseased pulp cavity, it is necessary to prevent bacterial proliferation within the root or pulp canal of the tooth by enlarging the canal without excessively weakening the root's wall by using endodontic files, bores, reamers or other instrumentation in order to: 1) mechanically remove as much of the root canal contents as is possible and 2) allow the introduction of irrigants into the root canal space that dissolve and disinfect organic debris, thus minimizing the presence of bacteria, as well as clearing the walls of the root canal of calcific debris created during instrumentation. After completing steps 1 and 2, the root canal is typically filled or obturated with a material such as gutta-percha and a sealer to occlude the pulp cavity and thus seal the root canal. This procedure is referred to as root canal therapy. Irrigation assists in removing debris and necrotic material remaining after the endodontic files, bores, and reamers used during the removing and shaping steps of the procedure. Although, the irrigant preferably is capable of dissolving or disrupting soft tissue remnants to permit their removal, the irrigant may be any suitable liquid such as water or various alcohols. More particularly, although some degree of debridement is preferred, any fluid may be used to flush debris from the root canal. General examples of appropriate irrigants include hydrogen peroxide and sodium hypochlorite. In order to ensure that as much of the debris and necrotic material as possible is removed, the irrigant is typically applied under pressure using a syringe and a needle inserted into the canal as shown in FIGS. 2A and 2B. However, as reported in Endodontics, 5th Edition, by John I. Ingle and Leif K. Bakland published June 2002, pages 502-503, it is important that the needle fit loosely in the canal to allow backflow. It is also reported that there is little flushing beyond the depth of the needle unless the needle is bound in the canal and the irrigant forcibly ejected, which is undesirable due to the danger of an irrigant such as sodium hypochlorite breaching the apex of the canal and entering the periapical tissue. However, unless the end of the needle is near the apex, the portion of the canal from the apex to the end of the needle cannot be effectively irrigated. But placing the end of the needle near the apex increases the likelihood of the irrigant, which is applied under pressure, entering the periapical tissue. This can be a source of post treatment endodontic pain for the patient. Furthermore, if a significant quantity of an irrigant like sodium hypochlorite is accidentally injected into the periapical tissue, morbid clinical complication can occur including excruciating pain, immediate swelling (ballooning) of the tissue, and profuse bleeding.

Existing techniques attempt to address this problem by using very small needles to get close to the apex while still fitting loosely in the canal to allow backflow or using an instrument to move some of the irrigant towards the apex with the irrigant no longer under pressure. However, neither technique completely solves the problem. Even the tip of the smallest needles that deliver irrigants under pressure must be kept a safe distance (approximately 4-6 mm) away from the apex in order to avoid accidentally forcing irrigants into the periapical tissue. This safety issue most often results in an area or zone between the apex and needle tip devoid of irrigant. Use of an instrument to force the irrigant through this zone towards the apex is very time consuming and also does not guarantee that the irrigant has flushed the canal all the way to the apex without going too far.

SUMMARY OF THE INVENTION

The present invention addresses the prior art problems of inadequate delivery of the irrigant to the apex of the canal resulting in an incomplete cleaning of the canal and penetration of the irrigant past the apex into the periapical tissue resulting in treatment complications. According to the invention, after the working of the canal by instruments to remove material and shape the walls of the canal, a cannula is inserted into the canal extending to about 5 mm from the apex and a vacuum is applied which begins to suck up the debris inside the canal. As this vacuum is applied, a small tube used to deliver irrigant is placed just inside the coronal opening of the root canal. Irrigant is passively flowed into the opening of the root canal, but not under pressure. As the irrigant is supplied, it is drawn to the source of the vacuum causing it to cascade down the walls of the root canals, into the tip of the cannula and out through the vacuum system. After several minutes of irrigant cascading down the canal walls, the cannula is removed and a second, smaller cannula with a hole in its wall near the tip is inserted into the canal until it virtually touches the apical tissue, but unlike the prior art, extending it past the apex does not cause irrigant to enter the periapical tissue because as soon as the hole enters the periapical tissue, since it is no longer in an open space, the vacuum created by the cannula is not present. In an alternate embodiment, instead of delivering irrigant via the cannula and applying a vacuum to the microcannula, the irrigant may be supplied via the microcannula. In this embodiment, a vacuum is applied via a tube which is inserted partway down the root canal. Tube and microcannula pass through a material created by a standard dental filling material of a composite nature which provides a seal at a position near the top of the coronal opening. The irrigant is supplied in a manner sufficient to ensure delivery to the side vent of the microcannula. The vacuum at the end of tube draws the irrigant and debris up from the apex of the root canal into the tube.

DETAILED DESCRIPTION

Figure 1:
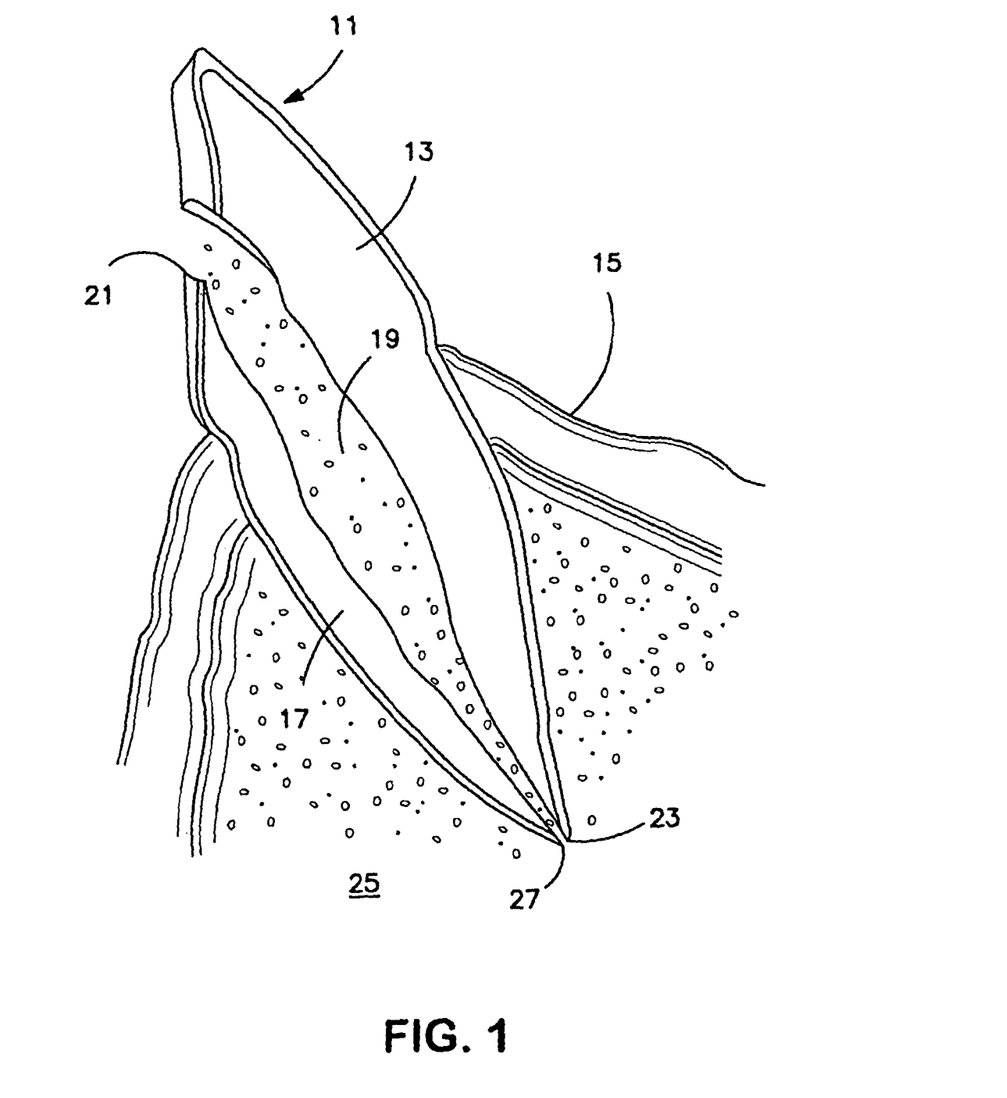
FIG. 1 is a cut away side view of a tooth showing its root canal and periapical tissue.

FIG. 1 illustrates a cutaway portion of a human tooth 11 as it may appear after a portion of a root canal procedure has been completed, namely wherein as much of the pulp material as is possible has been removed by instrumentation. The tooth 11 includes a crown portion 13 which is generally the exterior portion extending past gums 15. The interior portion of the tooth extending past the other side of gums 15 is referred to as the root 17. In approximately the middle of the root extending almost the entire length of the root is the root canal 19 which extends from one end 21 near the crown portion of the tooth to an apex 23 at the tip of root 17. As shown in FIG. 1, the non-visible portion of tooth 11 extending past gums 15 is surrounded by periapical tissue 25.

Of course, prior to the initiation of the root canal procedure, the apical foramen 27 located at or very near the root apex 23 is the only opening into the root canal.

After the instrumentation phase of the root canal procedure has been completed, there is a large quantity, both in terms of size and amount, of debris within the root canal.

According to the present invention, after the instrumentation step, cleansing of the root canal is performed in two phases. The first phase is referred to as gross evacuation of the coronal portion of the root canal which is the portion of the root canal 19 beginning approximately 4-5 mm from apex 23. The second phase is referred to as apical evacuation for cleaning the final 4-5 mm of the root canal.

Figure 3A:
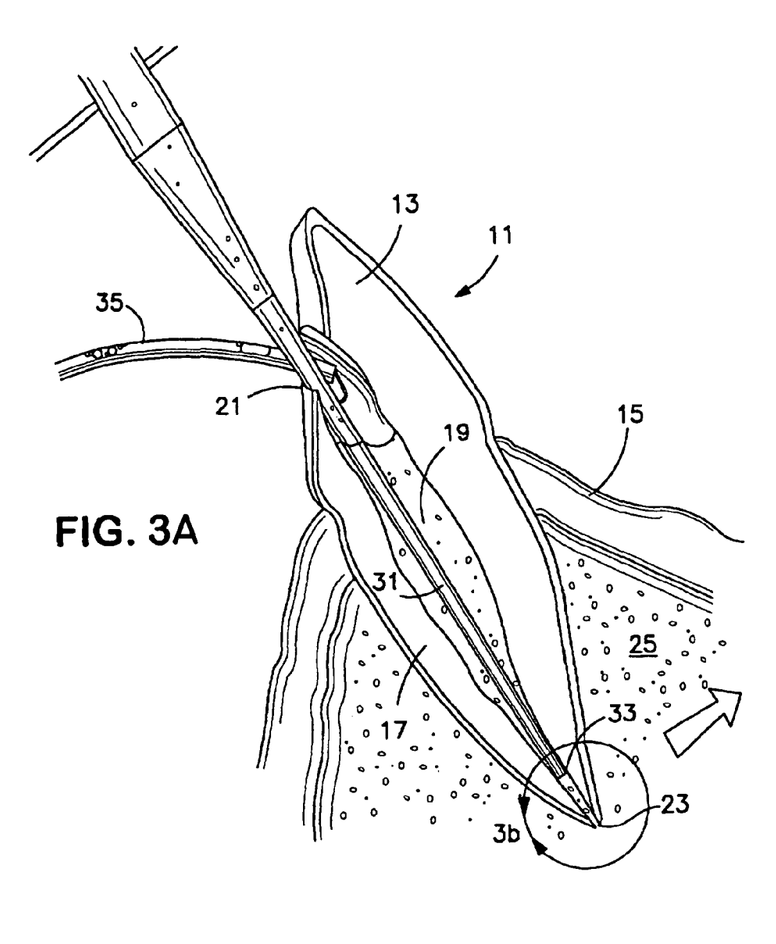
FIG. 3A is a cut away side view of a tooth showing a first cannula and fluid delivery tube.
Figure 3B:
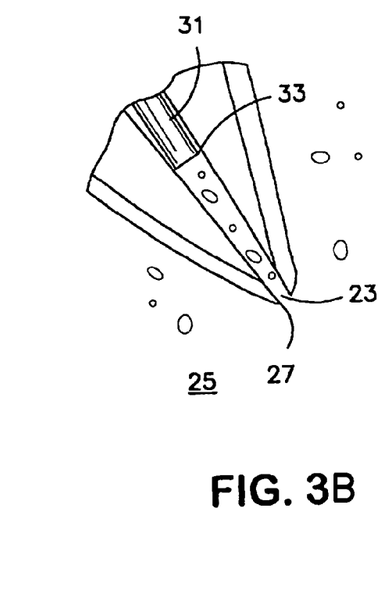
FIG. 3B is an expanded view taken along line 3b-3b of FIG. 3A.

Referring now to FIG. 3A, the methods and apparatus used for the gross evacuation of the coronal portion of the root canal will now be explained. A cannula 31 is inserted into the canal to a point 33 approximately 4-5 mm from the apex as seen in FIG. 3B. A suitable cannula for this purpose is a soft plastic cannula such as part number UP0341 available from Ultradent Products, Incorporated located in South Jordan, Utah. Of course, any comparable device may be used for this purpose. A vacuum is applied to the cannula as is well known in the art which results in debris being sucked up into the cannula. Specifics of a suitable delivery tube 35 and vacuum system are well known to persons skilled in the art.

A fluid delivery tube 35 is placed at the top of the coronal opening of the root canal at end 21 as shown in FIG. 3A and the desired irrigant is supplied by fluid delivery tube 35. A suction exists at point 33 of the cannula by virtue of an opening in the end of the tube adjacent to point 33 and the applied vacuum which results in the irrigant and remaining debris being drawn to the hole in the end of cannula at point 33. This irrigation and suction results in a nearly complete cleaning of the upper portion of the canal, i.e., the portion extending from the tip of the cannula at point 33 through the entire length of the canal to end 21. This occurs because as the irrigant is delivered via the delivery tube, the irrigant fills the root canal space combines with the debris and together are sucked down the root canal by virtue of the vacuum created at the end of delivery tube at point 33 and then up through cannula 31 by virtue of the vacuum created. This step normally takes several minutes to complete depending on the size of the root canal space. For example upper canine teeth have larger root canal spaces than lower incisors and require a longer initial irrigation. At the end of this phase the irrigant will be clear and devoid of gas bubbles formed by the dissolving necrotic tissue as well as particulate matter remaining from instrumentation.

It should be noted that although some irrigant may go past end 33, the 4-5 mm distance from apex 23 is sufficient to prevent any irrigant from reaching periapical tissue 25.

The gross evacuation of the canal debris in the upper portion of the root canal is critical to the proper completion of phase two since a much smaller tube is used to evacuate the apical portion, i.e., the bottom 4-5 mm of the root canal. This is because the debris in the upper portion of the root canal, prior to the evacuation performed by phase one, includes particles of a size which would clog the smaller opening of the microcannula which is inserted into the apical portion of the root canal.

Figure 4A:
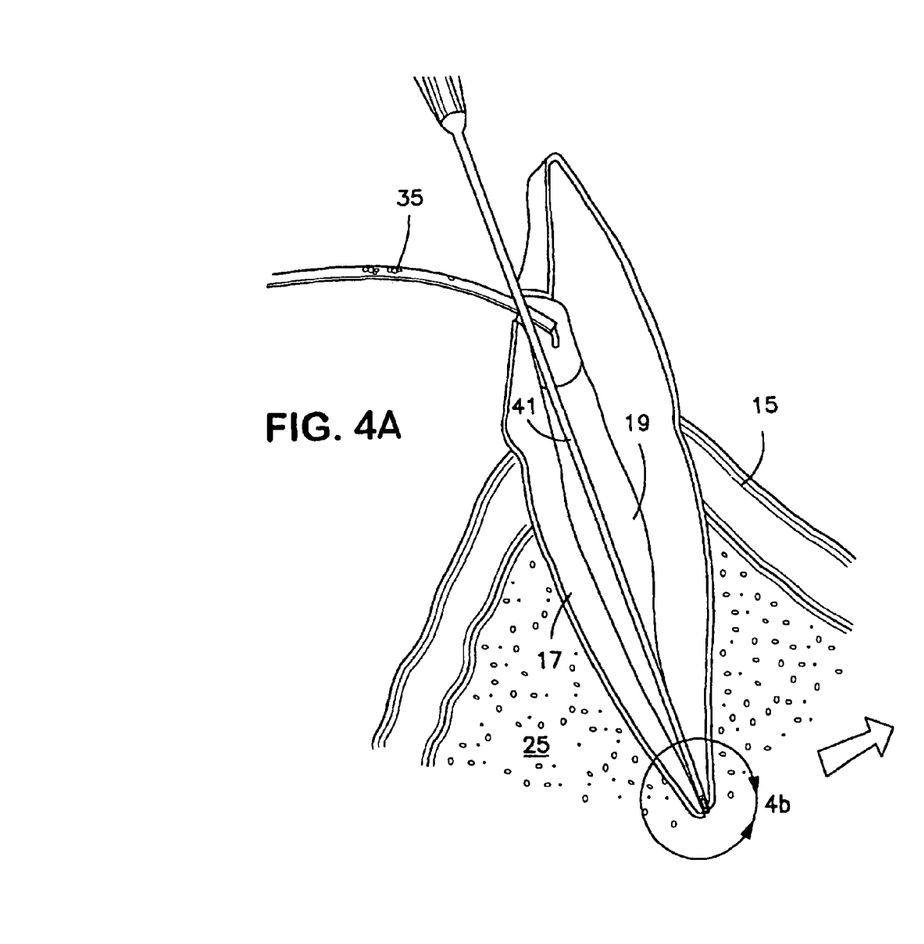
FIG. 4A is a cut away side view of a tooth showing a second cannula and fluid delivery tube.

Phase two of the procedure will now be described with references to FIGS. 4A and 4B. In phase two, a microcannula 41 is inserted into the root canal extending to the apex 23 as best seen in FIG. 4A. Microcannula 41 is typically made of a metallic material such as stainless steel or titanium and in one embodiment, has an outside diameter of 0.014 inches. Its tip 43 is welded shut and rounded and includes a side vent approximately 0.75 mm long beginning at a point approximately 0.5 mm from the end of tip 43.

Of course, the foregoing dimensions and materials are provided by way of example of a specific embodiment. What is important is that microcannula 41 be sized so as to be able to fit into the canal so that it extends substantially completely to apex 23 with side vent 45 extending as close to the end of the root as possible but without extending into the periapical tissue. Further, microcannula 41 should be sized so that there is close contact between the root canal wall in the apical portion and the microcannula. This is to ensure that some of the irrigant is drawn to the end of microcannula 41 by capillary action.

As was the case in phase one, irrigant is delivered via delivery tube 35 and a vacuum is applied to microcannula 41. In this manner, irrigant is drawn down into the root canal and into the apical portion of the root canal, that is, the bottom approximately 4-5 mm portion of the canal ending at apex 43. Since tip 43 is closed, irrigant is drawn into vent 45 and does not extend past tip 43 and cannot be drawn into apical tissue 25 due to the vacuum which exists at vent 45. By this technique, the irrigant flushes the apical portion of the root canal, removing out any remnants of debris which still exist in a manner which does not allow the irrigant to enter the periapical tissue.

Additionally, and importantly, in the event microcannula 41 is accidentally forced into the periapical tissue, the side vent will become obstructed by the tissue and the vacuum which exists in the root canal ceases to exist. Since the irrigant in the canal is not under pressure, the irrigant will cease to be withdrawn by microcannula 41 indicating to the practitioner that the microcannula has extended too far and needs to be withdrawn back into the root canal space slightly, up to the point when the side vent is not in the periapical tissue at which point the irrigant again begins to be withdrawn.

Figure 5:
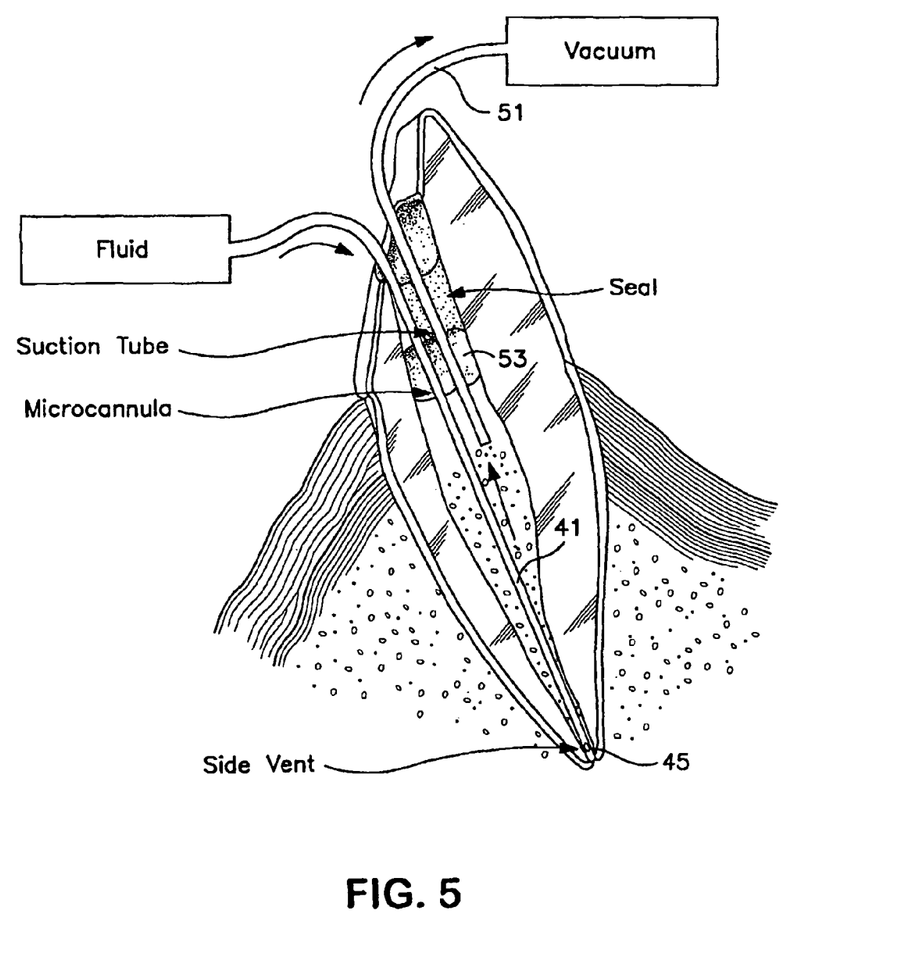
FIG. 5 is a cut away side view of a tooth showing an alternate embodiment of the invention illustrated in FIG. 4A.

In an alternate embodiment, and referring now the FIG. 5, instead of delivering irrigant via delivery tube 35 and applying a vacuum to microcannula 41, the irrigant may be supplied via the microcannula. In this embodiment, a vacuum is applied via a tube 51 which is inserted partway down the root canal. Tube 51 and microcannula 41 pass through a material created by a standard dental filling material of a composite nature (like the material used in white dental fillings) or alternately a standard dental impression material usually made of a silicone nature which provides a seal at a position near the top of the coronal opening. The irrigant is supplied in a manner sufficient to ensure delivery to the side vent 45 of the microcannula. The vacuum at the end of tube 51 draws the irrigant and debris up from the apex of the root canal into the tube.

In this alternate embodiment, the flow of the irrigant may be reversed from apex to crown by placing the microcannula adjacent to the apex, installing a vacuum tube into the canal near the coronal portion and sealing the canal coronally such that both and microcannula and vacuum tube are below the seal, with the vacuum tube being positioned more coronally. As a vacuum is applied to the coronal tube, irrigant is allowed to be drawn into the canal via the microcannula, then up the walls into the vacuum tube.

Figure 4B:
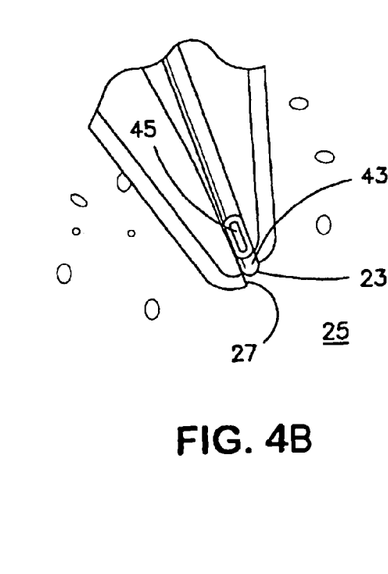
FIG. 4B is an expanded view taken along line 4b-4b of FIG. 4A.
Figure 6A:
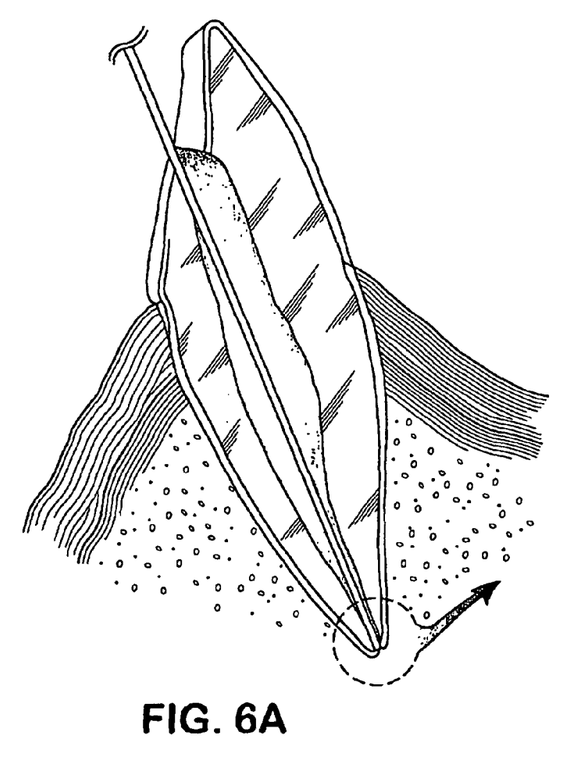
FIGS. 6A-6E show alternates embodiments of the side vent used by microcannula 41.
Figure 6B:
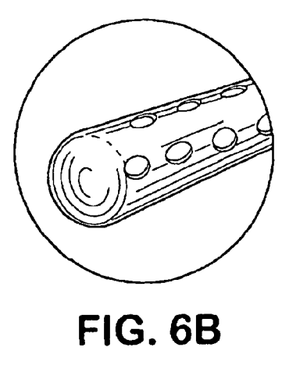
Figure 6C:
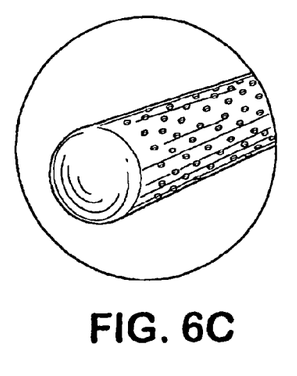
Figure 6D:
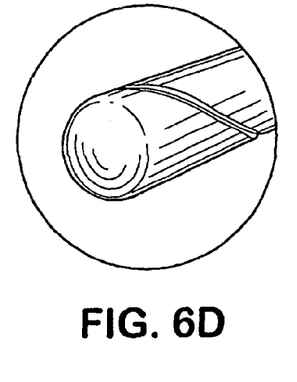
Figure 6E:
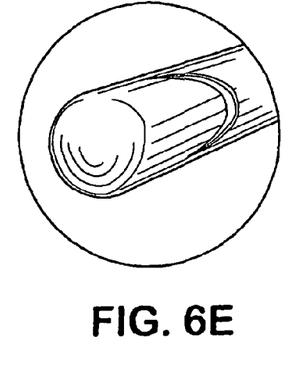

Referring now to FIGS. 6A-6E, side vent 45 instead of having a generally oblong shape as shown in FIG. 4B, may have a plurality of more round holes as shown in FIGS. 6A and 6C, a diagonal slit as shown in FIG. 6D or a U shaped slit as shown in FIG. 6E, or any other shape. In the FIG. 6B embodiment, the holes actually extend around the circumference of the microcannula. The diameter of the microcannula is 0.318 mm and the distance between the tip of the microcannula and the bottom of the hole nearest the tip is 0.22 mm. In one embodiment, the opening should not extend more than approximately 0.75 mm from the closed spherical tip of the microcannula, must be burr free and the opening must be smaller than the internal diameter of the microcannula to block any particles which clog the microcannula. The reasons the openings must be burr free is that the space where the microcannula is inserted is extremely restricted, and any burr extending from the opening is likely to scrape the dentin from the wall of the root canal and the resulting debris could clog the side vent opening(s). Usually, microcannula 41 is coupled directly to a tube used to provide the vacuum or supply the fluid.

Figure 7:
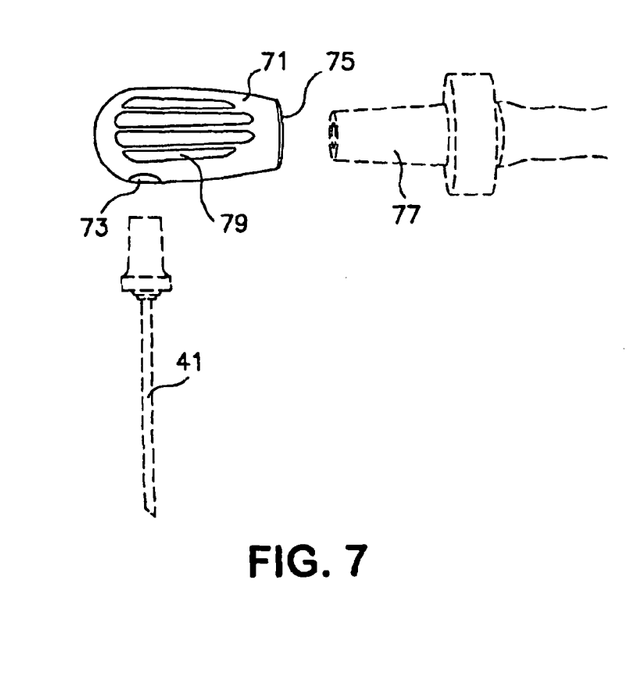
FIG. 7 shows a finger piece for use with the invention.
Figure 8:
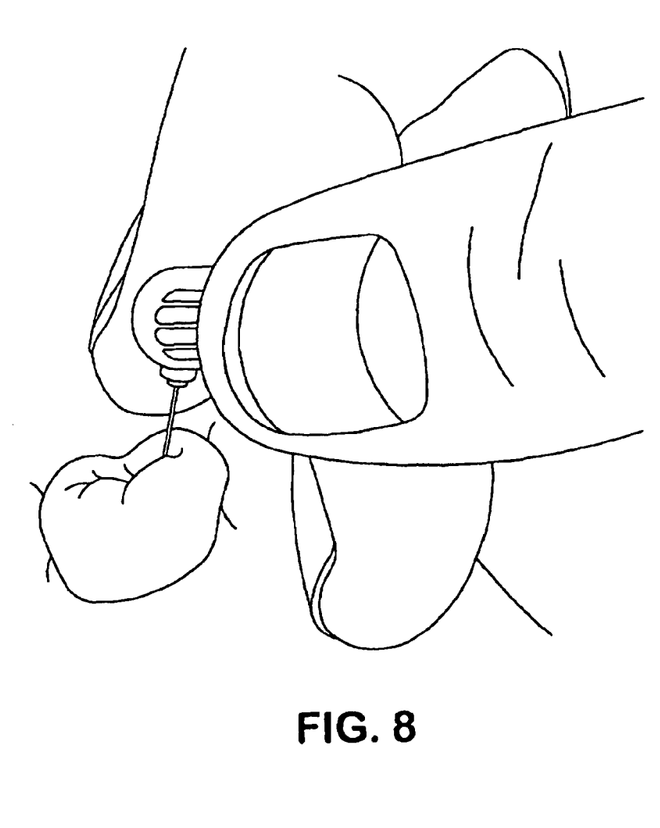
FIG. 8 shows how the finger piece of FIG. 7 is used.

FIG. 7 shows a finger grip handle 71 used to hold microcannula 41 (shown in shadow line). The finger grip handle has an opening 73 into which microcannula 41 is inserted. A second opening 75 arranged 90° from opening 73 receives a tube (shown in shadow line) which is connected to a device which produces the required vacuum or supplies the required fluid. Ridges 79 provide a grip to assist holding the handle between two fingers as shown in FIG. 8. Given the relatively small dimensions of microcannula 41 and the difficulty of maneuvering the microcannula within the confines of the mouth to perform the desired procedure, finger grip handle 71 provides extra leverage not available without the handle. In a preferred embodiment, finger grip handle is made of titanium. The two openings are sized to so that the microcannula and vacuum or fluid delivery device are held by friction.

Figure 9:
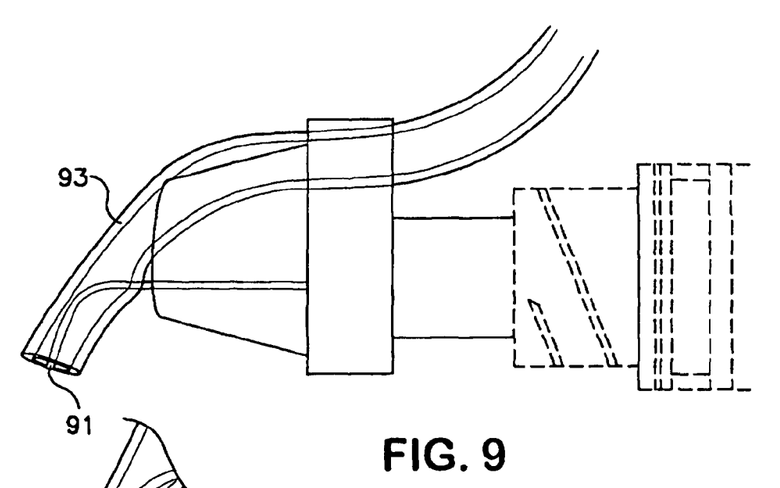
FIG. 9 shows a master delivery tip with syringe for use with the invention.
Figure 10:
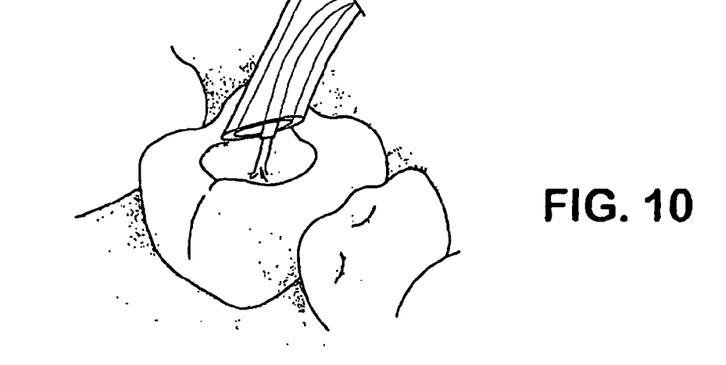
FIG. 10 shows how the master delivery tip of FIG. 9 is used.

FIG. 9 shows a master delivery tip. The delivery tip includes a metal tube 91 set into a molded fixture made of non-reactive plastic like nylon or polypropylene that is inserted on a standard luer lock fitting. The molded fixture holds a flexible plastic tube 93 non-reactive plastic like PVC over the metal tube, the other end being attached to a vacuum pump (not shown). During clinical use the clinician is able to add a fluid into the access cavity preparation of a root canal. When the level of the fluid being applied tube 91 reaches the top of the access cavity preparation, the excess is sucked away by a vacuum applied to tube 93 rather than spilling into the oral cavity (mouth). This feature allows the dentist or dental assistant to maintain a constant level of fluid in the root canal access cavity and is helpful throughout all aspects of root canal preparation including instrumentation and irrigation. FIG. 10 shows this operation wherein the fluid being applied is concurrently sucked away.

Figures 11A, 11B:
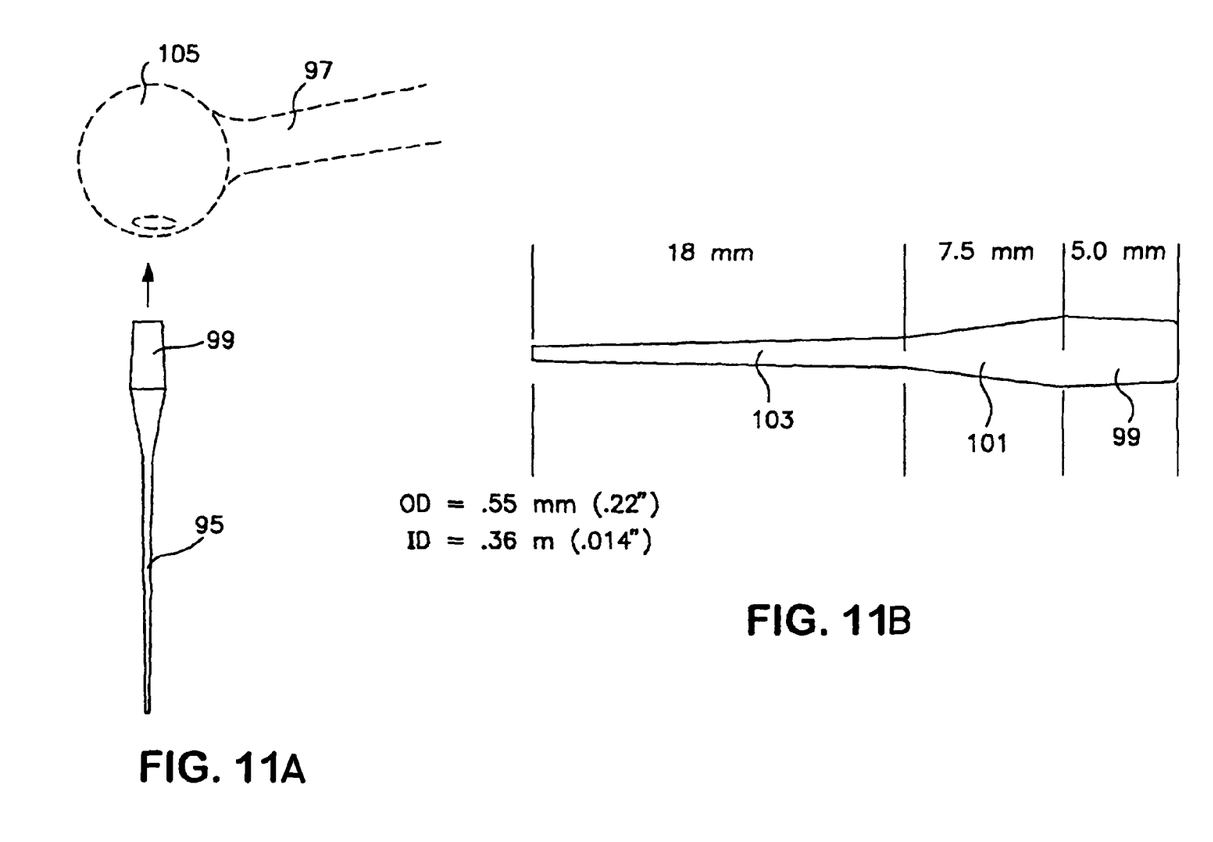
FIGS. 11A and 11B show the detail of a macro cannula or cannula for use with the invention.

FIG. 11A shows a specific design of a cannula 95 which may be used as cannula 31. A top portion 99 which is 5.0 mm in length has a slight taper for fitting into an opening in a handle 97 shown in shadow line in FIG. 11A and in more detail in FIG. 11B. A middle portion 101 which is 7.5 mm in length tapers to an outside dimension of 1 mm. A third portion 103 tapers from 1 mm to 0.55 mm at its end. The inside dimension at this end is 0.36 mm. While it is preferable that there be no flash at the end of the third portion, there is a 5% of inside diameter surface area maximum flash permitted at this point, since anything larger would serve to trap canal debris.

Figure 12:
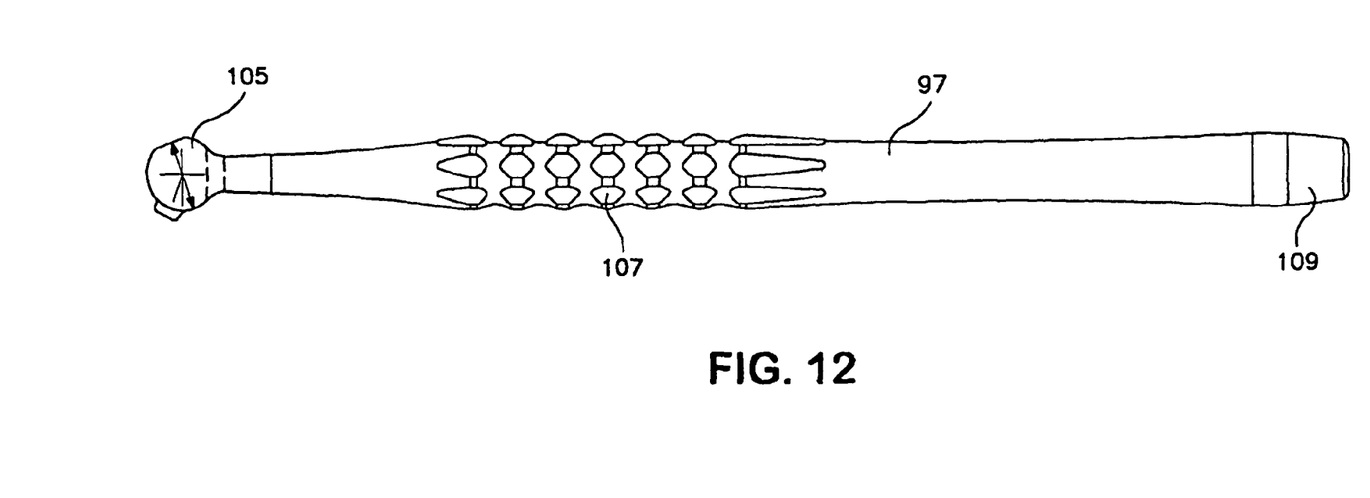
FIG. 12 shows a handle which may be used to hold the macro cannula shown in FIGS. 11A and 11B.

FIG. 12 shows handle 97 having head 105 sized to fit the top end of cannula 95 (or microcannula cannula 41 or 31) by friction. Raised elements 107 provide a finger grip. The opposite end 109 of handle 106 is sized to accept a tube from a vacuum unit (not shown).

What is claimed is:

1. A method for evacuating a root canal of a tooth, said tooth having a coronal end with an open access cavity and an apex end, the method comprising:
    delivering a fluid at said coronal end of said tooth;
    inserting a first cannula into said root canal such that a tip of said first cannula is located nearer said apex end of said tooth than the location at which said fluid is delivered;
    evacuating said fluid from said root canal through said first cannula to cause fluid flow in a direction from said coronal end toward said apex end;
    removing said first cannula from said root canal;
    inserting a second cannula into said root canal from said coronal end such that a tip of said second cannula is located nearer said apex end of said tooth than said tip of said first cannula; and
    evacuating said fluid from said root canal through said second cannula.

2. The method of claim 1 further comprising:
    evacuating said fluid from said coronal end of said tooth during evacuating said fluid from said root canal through said first cannula and/or during evacuating said fluid from said root canal through said second cannula.

3. The method of claim 1 wherein inserting said second cannula includes inserting said tip of said second cannula through an apical foramen of said root canal and then withdrawing said tip of said second cannula to a position in said root canal at which evacuating said fluid from said root canal through said second cannula starts.

4. The method of claim 1 wherein evacuating said fluid through said second cannula includes evacuating said fluid through one or more openings that are positioned around the circumference of said second cannula.

5. The method of claim 4 wherein said one or more openings are each smaller than the internal diameter of said second cannula.

6. The method of claim 1 wherein inserting said second cannula into said root canal includes inserting said second cannula having an outside diameter that is less than the outside diameter of said first cannula into said root canal.

7. The method of claim 1 further comprising:
   providing a source of vacuum at said open access cavity for evacuating said fluid from said coronal end of said tooth.

\* \* \* \* \*